(12) United States Patent
Joshi et al.

(10) Patent No.: US 8,591,472 B2
(45) Date of Patent: Nov. 26, 2013

(54) APPARATUS FOR ADMINISTERING A THERAPEUTIC AGENT INTO TISSUE USING A NEEDLE AS THE MATERIAL TREATMENT MODULE

(75) Inventors: Ashok V. Joshi, Salt Lake City, UT (US); James Steppan, Park City, IA (US); Jesse Nachlas, Salt Lake City, UT (US); Thomas A. Meaders, West Valley City, UT (US); Kieran P. Murphy, Toronto (CA)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

(21) Appl. No.: 13/189,290

(22) Filed: Jul. 22, 2011

(65) Prior Publication Data

US 2012/0022438 A1    Jan. 26, 2012

Related U.S. Application Data

(63) Continuation of application No. 11/616,041, filed on Dec. 26, 2006, now Pat. No. 8,066,659, which is a continuation-in-part of application No. 11/193,339, filed on Aug. 1, 2005, and a continuation-in-part of application No. 10/867,215, filed on Jun. 15, 2004, now Pat. No. 7,615,030.

(51) Int. Cl.
*A61M 37/00* (2006.01)
*A61M 5/00* (2006.01)

(52) U.S. Cl.
USPC .......................................... 604/187; 604/24

(58) Field of Classification Search
USPC ............... 604/23, 506, 24–26, 187, 239, 240, 604/257, 264, 272
See application file for complete search history.

(56) References Cited

U.S. PATENT DOCUMENTS

| | | | |
|---|---|---|---|
| 2,032,723 A | | 3/1936 | Schweser |
| 3,682,162 A | * | 8/1972 | Colyer .......................... 600/373 |
| 4,193,397 A | | 3/1980 | Tucker et al. |
| 4,485,815 A | | 12/1984 | Amplatz et al. |
| 4,632,980 A | | 12/1986 | Zee et al. |
| 4,644,960 A | | 2/1987 | Johans |

(Continued)

FOREIGN PATENT DOCUMENTS

| | | | |
|---|---|---|---|
| DE | 447936 | * | 7/1927 |
| DE | 2543284 | | 3/1977 |

(Continued)

OTHER PUBLICATIONS

Mayekar, Kishor "Non-Final Office Action", U.S. Appl. No. 12/816,787, (Sep. 25, 2012),1-6.

(Continued)

*Primary Examiner* — Bhisma Mehta
*Assistant Examiner* — Bradley Osinski
(74) *Attorney, Agent, or Firm* — David Fonda

(57) ABSTRACT

An apparatus for administering a therapeutic is provided. In various embodiments, the apparatus includes a syringe having a barrel and a plunger and having a material treatment module associated with a needle. The material treatment module may be an ozone generator that is initiated such that material containing ozone accumulates within the needle. The material can then be delivered from the barrel into a target site via the needle, thereby delivering therapeutic effects to that target site.

20 Claims, 7 Drawing Sheets

(56) References Cited

U.S. PATENT DOCUMENTS

| | | | |
|---|---|---|---|
| 4,743,199 A | 5/1988 | Weber et al. | |
| 4,938,233 A | 7/1990 | Orrison | |
| 5,052,382 A | 10/1991 | Wainwright | |
| 5,078,714 A | 1/1992 | Katims | |
| 5,106,589 A | 4/1992 | Conrad | |
| 5,163,904 A | 11/1992 | Lampropoulos et al. | |
| 5,439,452 A | 8/1995 | McCarty | |
| 5,536,241 A | 7/1996 | Zapol | |
| 5,540,898 A | 7/1996 | Davidson | |
| 5,674,195 A | 10/1997 | Truthan | |
| 5,797,872 A | 8/1998 | Ogata et al. | |
| 5,868,999 A | 2/1999 | Karlson | |
| 5,971,722 A | 10/1999 | Maget et al. | |
| 6,071,280 A | 6/2000 | Edwards et al. | |
| 6,073,627 A | 6/2000 | Sunnen | |
| 6,086,552 A | 7/2000 | Bolton | |
| 6,103,190 A * | 8/2000 | Tanimura et al. | 422/29 |
| 6,110,431 A * | 8/2000 | Dunder | 422/186.12 |
| 6,134,806 A | 10/2000 | Dhaemers | |
| 6,136,308 A | 10/2000 | Tremblay et al. | |
| 6,204,058 B1 | 3/2001 | Bolton | |
| 6,251,090 B1 | 6/2001 | Avery et al. | |
| 6,391,183 B1 | 5/2002 | Tanioka et al. | |
| 6,399,664 B2 | 6/2002 | Smith | |
| 6,413,228 B1 | 7/2002 | Hung et al. | |
| 6,620,379 B1 | 9/2003 | Piuk et al. | |
| 6,632,222 B1 | 10/2003 | Edwards et al. | |
| 6,800,064 B2 * | 10/2004 | Liang | 604/25 |
| 6,810,288 B2 | 10/2004 | Joshi | |
| 6,875,018 B2 | 4/2005 | Lynch et al. | |
| 6,912,417 B1 | 6/2005 | Bernard et al. | |
| 7,244,354 B2 | 7/2007 | Burris et al. | |
| 7,615,030 B2 | 11/2009 | Murphy et al. | |
| 8,066,659 B2 | 11/2011 | Joshi et al. | |
| 8,066,695 B2 | 11/2011 | Muto et al. | |
| 8,162,873 B2 | 4/2012 | Muto et al. | |
| 2002/0037235 A1 | 3/2002 | Khatchatrian et al. | |
| 2002/0133148 A1 | 9/2002 | Daniel et al. | |
| 2002/0188323 A1 | 12/2002 | Penner et al. | |
| 2003/0050674 A1 | 3/2003 | Joshi | |
| 2003/0084907 A1 | 5/2003 | Pacek et al. | |
| 2003/0176834 A1 | 9/2003 | Horth et al. | |
| 2004/0071615 A1 | 4/2004 | Khatchatrian et al. | |
| 2004/0092905 A1 | 5/2004 | Azzolini | |
| 2004/0133188 A1 | 7/2004 | Vardi et al. | |
| 2004/0245087 A1 | 12/2004 | Lee | |
| 2004/0254525 A1 | 12/2004 | Uber et al. | |
| 2005/0010069 A1 | 1/2005 | Fitchett et al. | |
| 2005/0023371 A1 | 2/2005 | Joshi et al. | |
| 2005/0074501 A1 | 4/2005 | Murphy et al. | |
| 2005/0203503 A1 | 9/2005 | Edwards et al. | |
| 2005/0277912 A1 | 12/2005 | John | |
| 2006/0095026 A1 | 5/2006 | Ricart et al. | |
| 2006/0166088 A1 | 7/2006 | Hokanson et al. | |
| 2006/0251551 A1 | 11/2006 | Johnson | |
| 2007/0025890 A1 | 2/2007 | Joshi et al. | |
| 2007/0154363 A1 | 7/2007 | Joshi et al. | |
| 2008/0004615 A1 | 1/2008 | Woloszko et al. | |
| 2008/0009847 A1 | 1/2008 | Ricart et al. | |
| 2008/0167650 A1 | 7/2008 | Joshi et al. | |
| 2009/0204062 A1 | 8/2009 | Muto et al. | |
| 2009/0209902 A1 | 8/2009 | Muto et al. | |
| 2010/0307928 A1 | 12/2010 | Joshi et al. | |
| 2010/0312171 A1 | 12/2010 | Joshi et al. | |
| 2012/0022437 A1 | 1/2012 | Joshi et al. | |
| 2012/0150173 A1 | 6/2012 | Joshi et al. | |

FOREIGN PATENT DOCUMENTS

| | | |
|---|---|---|
| JP | 08-150213 | 6/1996 |
| JP | 11-292512 | 10/1999 |
| JP | 2001506172 | 5/2001 |
| JP | 2005307232 | 11/2005 |
| WO | WO-96/08280 | 3/1996 |
| WO | WO-98/10774 | 3/1998 |
| WO | WO-01/50983 | 7/2001 |
| WO | WO-02/076533 | 10/2002 |
| WO | WO-2004103452 | 12/2004 |
| WO | WO-2005032387 | 4/2005 |

OTHER PUBLICATIONS

Osinski, Bradley J., "Notice of Allowance", U.S. Appl. No. 11/616,041, (Aug. 12, 2011),1-5.

Smith, Kaitlyn E., "Non-final Office Action", Non-final office action for U.S. Appl. No. 12/052,617, (Apr. 11, 2012),1-8.

Stigell, Theodore J., "Non-Final Office Action", Non-Final Office Action of U.S. Appl. No. 12/429,736, (Nov. 4, 2011),1-7.

Stigell, Theodore J., "Final Office Action", Final Office Action for U.S. Appl. No. 12/429,736, (Feb. 21, 2012),1-8.

Stigell, Theodore J., "Non-Final Office Action", Non-Final Office Action for U.S. Appl. No. 12/431,062, (Jan. 18, 2012),1-10.

Umehara, Makiko "Examiner's First Report (AU)", Examiner's First Report for AU application No. 2010206008 (corresponding to U.S. Appl. No. 12/429,736, (Feb. 24, 2011),1-2.

Umehara, Makiko "Examiners Report No. 2 (AU)", Examiners Report No. 2 (AU) for app. No. 2010204467 (corresponding to U.S. Appl. No. 12/430,740), (Mar. 29, 2012),1-2.

McTavish, Megan "Office Action (CA)", Office Action/Notification of Requisition (CA) for app. No. 2612541 (corresponding to U.S. Appl. No. 11/193,339, (Aug. 25, 2011),1-3.

Tanaka, Reiko "Notice of Reasons for Rejection", Notice of Reasons for Rejection (JP) and Translation for app No. 2009-544036 (corresponding to U.S. Appl. No. 11/616,041, (Jan. 24, 2012),1-8.

Pfeiffer, Uwe "EP Search Report", App. No. 09722670, (Jun. 17, 2011),1-6.

Stigell, Theodore "USPTO Office Action", U.S. Appl. No. 12/430,740, (Aug. 12, 2011),1-9.

Stigell, Theodore J., "Non-Final Office Action", U.S. Appl. No. 12/431,062, (Jul. 11, 2012),1-8.

Schell, Laura C., "Non-Final Office Action", U.S. Appl. No. 11/193,339, (Jul. 20, 2012),1-9.

Singh, Vijay "Examiner's First Report on Patent Application 2007342491", Australian Patent Application 2007342491, (May 15, 2012),1-3.

McTavish, Megan "Notice of Requisition", CA App. No. 2,612,541 (Corresponding to U.S. Appl. No. 11/193,339), (Jul. 9, 2012),1-2.

"List of Medizone Patents and Trademarks", http://www.medizoneint.com/patents.html, 1-2.

"Translation of DE2543284", European Patent Office Automated Translation,(Oct. 5, 2007),1-4.

"Translation of Japanese Office Action", JP App. No. 2008-525006, (Jun. 21, 2011),1-11.

Andreula, Cosma et al., "Interventional Spinal Procedures", *European Journal of Radiology* 50, (2004),112-119.

Andreula, Cosma F., et al., "Minimally Invasive Oxygen-Ozone Therapy for Lumbar Disk Herniation", *American Journal of Neuroradiology* 24, (2003),996-1000.

Bocci, V. "Biological and Clinical Effects of Ozone. Has Ozone Therapy a Future in Medicine?", *British Journal of Biomedical Science* 56, (1999),270-279.

Bocci, V. et al., "Ozone in Medicine", *Ozone Science & Engineering* 23, (2001),207-217.

Bocci, Velio "Oxygen-Ozone Therapy: A Critical Evaluation", *Kluwer Academic Publishers: The Netherlands*, (2002),43-46.

Bocci, Velio "Ozone:A New Medical Drug", *Springer: The Netherlands*, (2005),9-11.

Bumgarner, Melba "Non-Final Office Action", U.S. Appl. No. 11/616,041, (Mar. 10, 2010),1-12.

Bumgarner, Melba "Office Action for U.S. Appl. No. 11/616,041 Mailed on Sep. 17, 2009", 1-7.

Jeon, Chang "International Search Report", PCT Application No. 2009/037413, (Nov. 3, 2009),1-4.

Jeon, Chang "Written Opinion of the International Searching Authority", PCT Application No. 2009/037413, (Nov. 3, 2009),1-5.

(56) References Cited

OTHER PUBLICATIONS

McCabe, Ed "Scientific and Medical References Proving Ozone's Validity as a Medical Treatment", <http://www.ozonetherapy.co.uk/articles/ed_mccabe_ozone_history_and_references.htm>, 1994, Retrieved Oct. 7, 2004,(1994).

Morello, Gaetano "Ozone Therapy: New Breakthrough for Back Treatment", http://allergytalk.com/6/ca_3.htm, Retrieved Oct. 8, 2007.,1.

Muto, Mario et al., "Percutaneous Treatment of Herniated Lumbar Disc by Intradiscal Oxygen-Ozone Injection", *Interventional Neuroradiology* 4:279-286, 1998, (1998),279-286.

Osinski, Bradley "Office Action for U.S. Appl. No. 11/616,041", (May 25, 2011),1-9.

Osinski, Bradley J., "Office Action for U.S. Appl. No. 11/616,041", (Nov. 5, 2010),1-11.

Schell, "Office Action for U.S. Appl. 11/193,339 sent Dec. 3, 2008",1-10.

Schell, Laura "Final Office Action", U.S. Appl. No. 11/193,339, (Jul. 14, 2010),1-12.

Schell, Laura "Non-Final Office Action", U.S. Appl. No. 11/193,339, (Jan. 19, 2010),1-9.

Schell, Laura "Office Action for U.S. Appl. No. 11/193,339 Mailed Jul. 6, 2009",1-9.

Schell, Laura C., "Office Action for U.S. Appl. No. 11/193,339", (Dec. 3, 2008),1-10.

Schultz, O "Abstract and International Search Report for WO2005032387", (Mar. 2, 2005),1-6.

Schultz, O "PCT International Search Report for PCT/IB2004/003706", (Jun. 3, 2005),1-6.

Schultz, O "PCT Written Opinion of the International Searching Authority for PCT/IB2004/003706", (Jun. 3, 2005),1-10.

Schultz, Ottmar "European Office Action for App. No. EP 08/004372 Completed May 8, 2008", 1-8.

Schultz, Ottmar "European Office Action for App. No. EP08/004367 Completed May 7, 2008", 1-6.

Stigell, "Office Action for U.S. Appl. 10/867,215 sent Oct. 16, 2008",1-6.

Stigell, "Office Action for U.S. Appl. No. 10/867,215 sent Apr. 1, 2008",1-8.

Stigell, Theodore "Non-Final Office Action", U.S. Appl. No. 12/430,740, (May 26, 2010),1-8.

Stigell, Theodore J., "Notice of Allowability for U.S. Appl. No. 10/867,215 Mailed Apr. 7, 2009", 1-4.

Stigell, Theodore J., "Notice of Allowability for U.S. Appl. No. 10/867,215 Mailed on Aug. 6, 2009", 1-4.

Stigell, Theodore J., "Office Action for U.S. Appl. No. 12/430,740", (Oct. 14, 2010),1-11.

Stigell, Theodore J., "Office Action for U.S. Appl. No. 12/430,740", (Feb. 22, 2011),1-6.

Stigell, Theodore J., "Office Action for U.S. Appl. No. 12/431,089", (Feb. 18, 2011),1-7.

Sunnen, Gerard "Ozone in Medicine Bibliography", http://www.medizoneint.com/biblio.html, (Sep. 1999),1,3,5,7.

Williams, Catherine S., "Office Action for U.S. Appl. No. 10/867,215", (Aug. 17, 2007),1-2.

Williams, Catherine S., "Office Action for U.S. Appl. No. 10/867,215", (Jul. 18, 2007),1-8.

Young, "International Search Report for PCT/US07/25989 sent Mar. 27, 2008",1-2.

Young, "Written Opinion for PCT/US07/25989 sent Mar. 27, 2008",1-6.

Young, Lee W., "PCT International Search Report for PCT/US06/28425", (Jul. 31, 2007),1-2.

Young, Lee W., "PCT Written Opinion of the International Searching Authority for PCT/US06/28525", (Jul. 31, 2007),1-4.

Osinski, Bradley J., "Non-Final Office Action", U.S. Appl. No. 13/188,999, (Dec. 14, 2012),1-7.

Viidebaum, Mikk "Extended European Search Report", EP App. No. 087863148.8 (corresponding to U.S. Appl. No. 11/616,041), (Nov. 28, 2012),1-8.

Unknown Japanese Examiner, "Notice of Reasons for Rejection", JP App. No. 2011-278004, (Feb. 12, 2013),1-2.

Okada and Associates, "Translation of Notice of Reasons for Rejection", JP App. No. 2011-278004, (Feb. 14, 2013),1-2.

Unknown, "Machine Translation of JP 08-150213", JP Patent publication 08-150213, (Jun. 11, 1996),1-6.

Izumi, et al., "English Abstract for JP 11-292512", Japanese Patent publication JP 11-292512, (Oct. 26, 1999),1-2.

Unkown Japanese Patent Examiner, "Notice of Reasons for Rejection", JP App. No. 2011-500900 (Corresponding to U.S. Appl. No. 12/052,617), (Feb. 5, 2013),1-3.

Okada and Associates, "Translation of Notice of Reasons for Rejection", JP App. No. 2011-500900 (Corresponding to U.S. Appl. No. 12/052,617), (Feb. 13, 2013),1-2.

Walsh, et al., "English Abstract for JP2001506172", Espacenet English Abstract for WO9904850, Corresponding to JP Patent Publication JP 2001506172, (May 15, 2001),1.

Maeda, et al., "English Abstract for JP2005307232", Espacenet English Abstract for JP2005307232, (Nov. 4, 2005),1-2.

Schell, Laura C., "Non-Final Office Action", U.S. Appl. No. 11/193,339, (Mar. 26, 2013),1-8.

\* cited by examiner

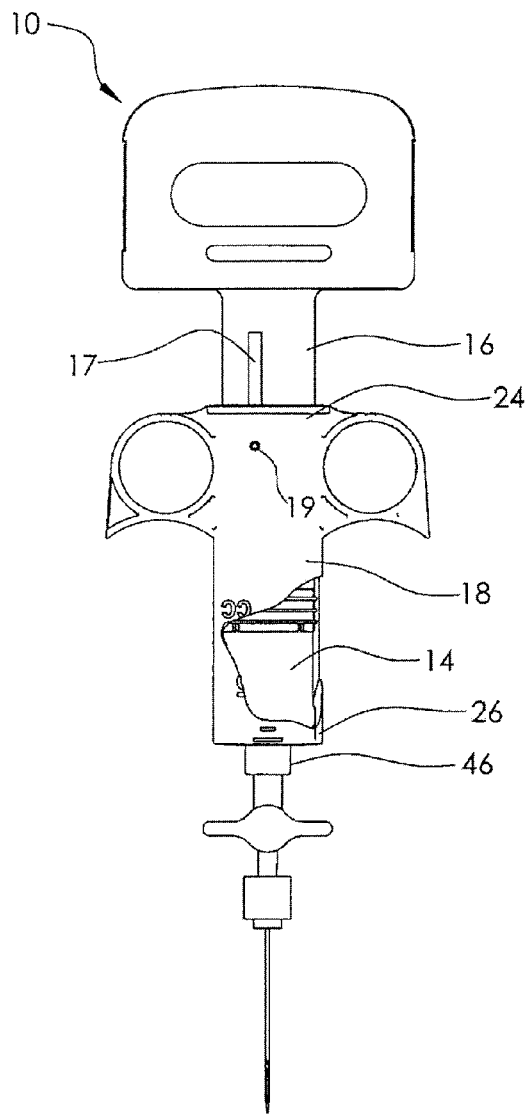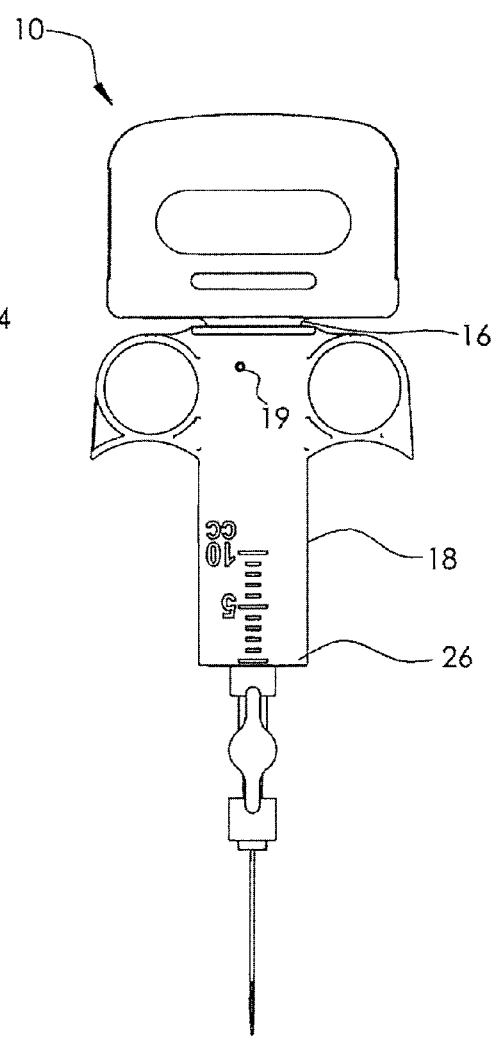
Fig. 5a                    Fig. 5b

SECTION A-A

DETAIL B

SECTION A-A

DETAIL B

APPARATUS FOR ADMINISTERING A THERAPEUTIC AGENT INTO TISSUE USING A NEEDLE AS THE MATERIAL TREATMENT MODULE

RELATED APPLICATIONS

This application is a continuation of, and claims priority to, U.S. patent application Ser. No. 11/616,041 entitled "Apparatus and Method for Administering a Therapeutic Agent into Tissue" and filed on Dec. 26, 2006 for Ashok Joshi, et al. which is a continuation-in-part of, and claims priority to, U.S. patent application Ser. No. 11/193,339 entitled "Apparatus and Method for Administering a Therapeutic Agent into Tissue" and filed on Aug. 1, 2005 for Ashok Joshi, et al. U.S. patent application Ser. No. 11/616,041 is also a continuation-in-part of, and claims priority to, U.S. patent application Ser. No. 10/867,215 entitled "Apparatus and Method for Administering a Therapeutic Agent Into Tissue" and filed on Jun. 15, 2004. These applications are incorporated herein by reference.

FIELD OF THE INVENTION

The present invention relates generally to an apparatus for administering a therapeutic agent into tissue and in particular, for the creation and administration of a fluidic therapeutic agent into a tissue using a portable device.

BACKGROUND OF THE INVENTION

Back joint disc or tendon pain is a common and potentially debilitating ailment that affects an estimated 80% of the worldwide population at least once in a lifetime. In many instances, the cause of the pain can be attributed to a degenerated intervertebral disc that has further deteriorated into a condition known as disc herniation. This occurs when the disc nucleus pulposus extrudes through a tear or fissure in the outer lining of the disk, thereby exerting pressure on spinal nerves. The compression caused by the herniated nucleus leads to inflammation and is directly responsible for the pain felt down the leg (also referred to as sciatica). Available treatments for this type of back pain vary according to the severity of the hernia. If mild, the patient's condition can be appeased with rest and inactivity for an extended period of time. However, for patients suffering from a severe herniation or who do not respond to non-invasive treatment (pharmacological and/or physical therapy), surgical intervention is often recommended. With this invasive treatment come several disadvantages such as:
  i) irreversibility of the procedure
  ii) formation of scar tissue
  iii) slower recovery time
  iv) longer hospital stays
  v) risk of infection Since the late 1950s, many attempts have been made to treat sciatica and lower back pain with minimally invasive percutaneous procedures to avoid surgery. Well known treatments for example are percutaneous discetomy, percutaneous plasma disc decompression (nucleoplasty), intradiscal electrothermal therapy (IDET), and percutaneous intradiscal radiofrequency thermocoagulation (PIRT) but the high costs of these procedures has kept researchers looking for another alternative. In 1984 an Italian orthopedic surgeon named Dr. Cesare Verga proposed the use of ozone/oxygen mixtures to treat the pathology of a herniated disk.

In other situations such as rheumatoid arthritis, osteoarthritis or a repetitive injury through sports or occupation, such as tennis elbow, frozen shoulder, or house maids knee, inflammation can develop between the two surfaces that are involved in allowing joint function, such as a tendon and the sheath or lubricated tube in which that tendon moves. Inflammation such as bursitis in the knee shoulder hip, or other anatomic bursa may benefit from the administration of a therapeutic agent such as oxygen-ozone mixtures or excited, energetic, pure oxygen, this includes epicondylitis, and other tendonitis and bursitis, including the wrist, hand and the tendon sheaths of the hand and wrist. Inflammation can occur at a site where a tendon or a ligament insert to bone or pass through a sheath from trauma, tension, over use or disease.

Inflammation can develop through pathologies of any joint, and these may again include the inflammatory arthropatic conditions of rheumatoid arthritis, psoriatic arthritis and the like, or osteoarthritis. Joints that may be involved in these processes that are amenable to the administration of a therapeutic agent such as oxygen-ozone mixtures or excited, energetic, pure oxygen include the synovial joints such as the, temperomandibular joint, the hip joint, knee joint, ankle joint, elbow joint or sacro-iliac joint. Vertebral facet and sacro-iliac joints may also benefit, inflammatory involvement of joints in the hand, wrist and feet with rheumatoid arthritis, osteoarthritis or a repetitive injury through sports or occupational such as carpal tunnel syndrome.

The inflammatory and arthritic or degenerative discussions described above are usually treated with a combination of anti-inflammatory agents such as ibuprofen, or more powerful drugs such as steroids or chemotherapy such as methotrexate. It is a common medical practice to inject steroid medications or lidocaine directly into the inflamed tissue or joint. This is often done repeatedly. These drugs can be associated with side effects of infection and even death from gastric ulcer bleeding or immunosuppression and infection. We believe that ozone therapy whether with oxygen-ozone mixtures or excited, energetic, pure oxygen as a gas or dissolved in a liquid has advantages over the current practice.

Lavage of a surgical space prior to placement of a permanent surgical implant such as a hip or knee prosthesis, or pacemaker or treatment of an infected joint can be facilitated by the use of oxygen-ozone mixtures or excited, energetic, pure oxygen as a sterilizing substance. Similarly a colostomy stoma can be created such that the adhesive disk is infused with oxygen-ozone mixtures or excited, energetic, pure oxygen as a gas or dissolved in a liquid to aid in healing and inhibit infection. The post surgical recovery from sternotomy after cardiac surgery is often complicated by wound infection. Placement of a resorbable catheter in the wound that could be irrigated with oxygen-ozone mixtures or excited, energetic, pure oxygen as a gas or dissolved in a liquid would aid healing. Indeed any wound could have a resorbable multisided hole catheter placed in it to allow oxygen-ozone mixtures or excited, energetic, pure oxygen to be injected through it. This would have anti-infective, analgesic, and wound-healing properties thereby shortening recovery time and decreasing complication rates after surgery.

Endoscopic procedural infusion of ozone and trans catheter infusion of ozone can be used to inhibit the complications endoscopic medical intervention or image guided or non-image guided catheter based intervention for example in endoscopic evaluation of the pancreatic duct.

Dental injection of oxygen-ozone mixtures or excited, energetic, pure oxygen as a gas or dissolved in a liquid may augment the preparation and repair of dental cavities, and aid in reduction of root canal inflammation or periodontal disease.

There are veterinary applications of minimally invasive administration of oxygen-ozone mixtures or excited, energetic, pure oxygen as a gas or dissolved in a liquid in animals diseased with disc and degenerative syndromes. Few other options are available in that arena. Some animals are destroyed due to debilitating pain secondary to pain from disc disease, and arthritis.

Thus, there is a need for equipment specifically designed for the treatment of disc herniation and other medical conditions affecting the body with oxygen-ozone mixtures or excited, energetic, pure oxygen so that it can be done in an efficient and sterile manner. There is a need to develop kits for intervention in inflammatory and degenerative disease, that are portable, disposable, or reusable, but aid in creating sterile, stable, ozone rapidly on demand.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the scope of the present disclosure, the embodiments will be described and explained with specificity and detail in reference to the accompanying drawings in which:

FIG. 5a is a plan view of the apparatus shown in FIG. 1 in a fill position;

FIG. 5b is a plan view of the apparatus shown in FIG. 5a in a dispensing position;

FIG. 6a is a cutaway plan view of an alternative embodiment of the invention;

FIG. 6b is cross-sectional plan view of FIG. 6a taken along line A-A;

FIG. 6c is detailed plan view of section B of FIG. 6a;

FIG. 7c is detailed plan view of section B of FIG. 7a.

DETAILED DESCRIPTION OF THE INVENTION

The present invention may be embodied in other specific forms without departing from its spirit or essential characteristics. The described embodiments are to be considered in all respects only as illustrative and not restrictive. While the various aspects of the embodiments are presented in drawings, the drawings are not necessarily drawn to scale unless specifically indicated. The scope of the invention is, therefore, indicated by the appended claims rather than by the foregoing description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

In the following description, numerous specific details are provided, such as examples of housings, barriers, chambers etc., to provide a thorough understanding of embodiments of the invention. One skilled in the relevant art will recognize, however, that the invention can be practiced without one or more of the specific details, or with other methods, components, materials, and so forth. In other instances, well-known structures, materials, or operations such as vacuum sources are not shown or described in detail to avoid obscuring aspects of the invention.

Figure 1:
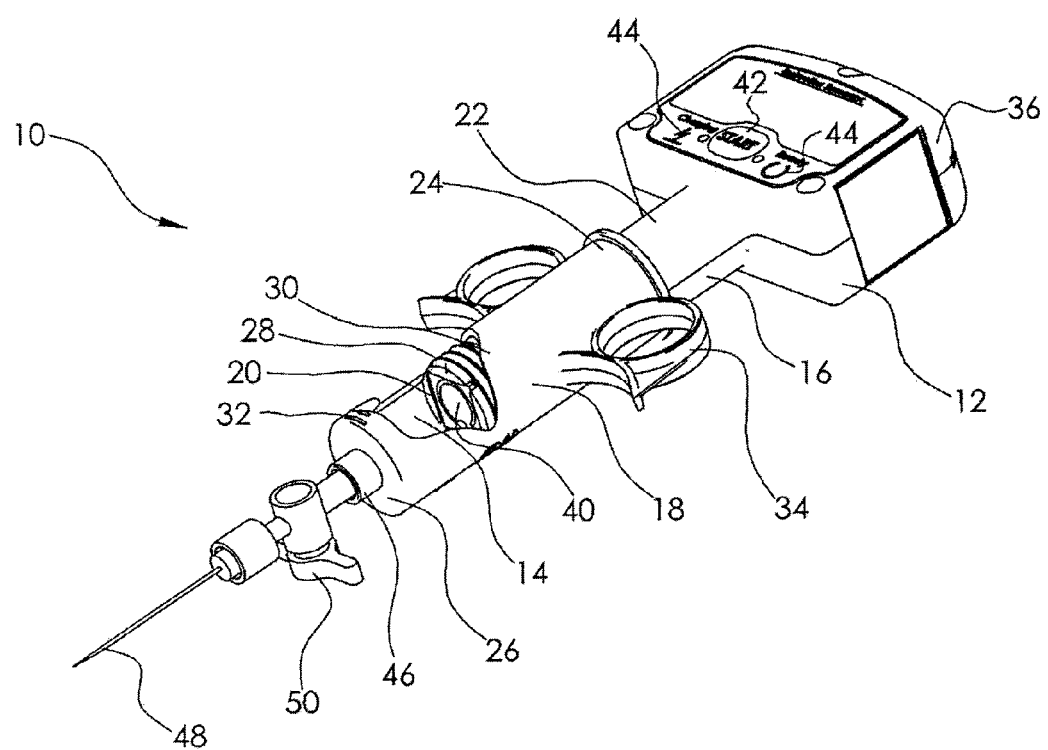
FIG. 1 is a partially cutaway perspective view of an apparatus for administering a therapeutic agent in accordance with an embodiment of the invention.

Referring now to the FIG. 1, a handheld dispensing apparatus 10 according to the present invention is shown. The apparatus 10 includes a housing 12 that defines a chamber 14. In one embodiment, the apparatus 10 or housing 12 includes a plunger 16 and a barrel 18 that define the chamber. The plunger has a first end 20 and a second end 22. The barrel 18 has a first end 24 that is open for receiving the first end 20 of the plunger 16 such that the barrel 18 movably engages the plunger 16. The barrel 18 also includes a second end 26. In the illustrated embodiment, the first end 20 of the plunger 16 and the second end 26 of the barrel 18 form the chamber 14. The housing 12 may have a volume of less than about 150 cubic centimeters. In one embodiment, the chamber 14 can hold a volume of material up to about 150 cubic centimeters. In another embodiment, the chamber 14 can hold a volume of no less than about 0.1 cubic centimeters. It will be appreciated that the range of volumes may coincide with the position of the plunger 16 within the barrel 18. For example, the plunger 16 may move within the barrel 18 between a fill position, where the first end 20 of the plunger 16 is within the first end 24 of the barrel 18, but not completely within the barrel 18, and a dispensing position, where the first end 20 of the plunger 16 is substantially within the barrel 18 such that the first end 20 of the plunger 16 is adjacent the second end 26 of the barrel 18.

The chamber 14 is configured to retain a material. "Material," as used throughout this specification, means gas, liquid, gels, solids, or combinations thereof. Material may also be solids suspended or dispersed throughout liquids, gases, or gels. A precursor or starting material may be charged into the device to be treated by operation of the device to create a beneficial or therapeutic agent. Accordingly, the device 10 can be used to create treated material that acts as a beneficial agent. As used throughout this disclosure, "precursor," "precursor material," and "starting material" are used synonymously. Additionally, "treated material," "beneficial agent," and "therapeutic agent" may be used synonymously. The device is used to make a precursor material into a beneficial agent and then deliver the beneficial agent to a desired place, usually within a body.

In one embodiment, the first end 20 of the plunger may be configured with a seal 28 to facilitate retention of the material within the chamber 14. The seal may be a gasket or flexible flange or other mechanical means known in the art. It will be appreciated by those of skill in the art that there are a variety of ways to retain material within the chamber 14, each of which are within the scope of this invention. An outer surface 30 of the barrel 18 may include graduations 32 to measure the amount of material in the chamber 14. The device 10 may be configured in such a way to facilitate moving the plunger 16 between the fill position and the dispensing position. For example, the barrel 18 may include a handle finger holds 34 and the plunger 16 may be configured with a handle 36.

In one embodiment, the apparatus 10 includes a material treatment module 40. As will be discussed in greater detail in connection with FIGS. 3 and 4 below, the material treatment module 40 can take a variety of configurations. The material treatment module 40 may be positioned within the housing 12 or the barrel 18. In one embodiment, the material treatment module 40 is positioned within the plunger 16. In other embodiments, the material treatment module 40 may be positioned within the barrel 18. In still other embodiments, the material treatment module 40 may be positioned outside the housing 12.

The material treatment module 40 is in operable communication with the chamber 14 such that precursor material in the chamber may come into contact with, and be treated by, the material treatment module 40. As used throughout this specification, the treating or treatment of material means to alter the composition or properties of all or a portion of the material. Similarly, "treated material" means material that has had its chemical composition or other properties altered or modified. For example, in an embodiment where the precursor material is oxygen, the material treatment module 40 may an ozone generator for creating ozone and the resulting or treated material may be a mixture of oxygen and ozone. Similarly, where the precursor material is water, the material treatment module 40 may oxidize water to produce a treated material the consists of oxygen and ozone. Where the precursor material is an aqueous salt solution, the material treatment module 40 may oxidize the ions in the solution to create a beneficial or therapeutic agent dissolved in the solution or emitted as a gas. For example, chloride ions in a precursor material may, after interaction with the material treatment module 40, become chlorine gas under the reaction

$$2Cl^- \rightarrow Cl_2 \quad (1)$$

which can then be expelled from the device into a desired location to apply its beneficial effects. Similarly, bromide ions may become bromine under the reaction

$$2Br^- \rightarrow Br_2 \quad (2)$$

Conversely, the material treatment module may be able to reduce the precursor material to form the beneficial or therapeutic treated material.

It will be appreciated that the original or precursor material may be treated by the material treatment module 40 to alter a variety of characteristics of the precursor material, including without limitation, the concentration of a particular element such as oxygen, the pH of the material, the temperature of the material, the viscosity of the material, and the like. The material treatment module 40 is able to take a benign material that is easy to store, and create a reactive material that has therapeutic value. Furthermore, treating the material may be accomplished by a variety of methods, including without limitation, reducing the material, oxidizing the material, electrochemically altering the material, chemically altering the material, thermally altering the material, or using light to alter the material. It will be appreciated that material treatment module the treated material may be a beneficial agent with various properties, characteristics, or attributes that may be therapeutic to a user. The apparatus 10 allows for transportable, single or multiple point-of-use application of the beneficial agent.

As will be discussed in greater detail below in connection with FIG. 2, the apparatus 10 may also have means for controlling the liquid treating module 40. For example, the device 20 may have an on/off switch 42 or other regulators. Additionally, the apparatus 10 may include visible and/or audible displays or indicators 44 to help the user determine a status of the liquid treating module. For example, the apparatus 10 may indicating when apparatus is treating material or when it has stopped treating material. It may also indicate whether treated material is in the chamber 14.

The housing 12 may have an outlet 46 in material communication with the chamber 14 for releasing the treated material from the housing 12. In one embodiment, the outlet 46 is a port configured in the second end 26 of the barrel 18. The outlet 46 may be configured to receive a needle 48. For example, the outlet 46 may allow a needle 48 to be press fit into the outlet 46. The outlet 46 may also be threaded to receive a threaded end to the needle 48. The needle 48 may be attached to the outlet 46 by a Luer or other mechanical connection or fitting. It will be appreciated by those of skill in the art that the outlet 46 and needle 48 may be configured in a variety of ways in order to communicate with each other. The needle is in material communication with the outlet and thus, the chamber allows treated material to enter into the body and a specific site that will provide the most therapeutic value to the user.

The apparatus 10 may also include a valve 50 to help control the movement of material between the chamber 14 and the needle 48. In one embodiment, the valve is a stopcock valve. The valve may be positioned in closed state while material is being treated to prevent leakage of the material. Once a predetermined amount of material is treated, the valve may be positioned in an open state to allow the treated material to exit the apparatus 10.

Figure 2:
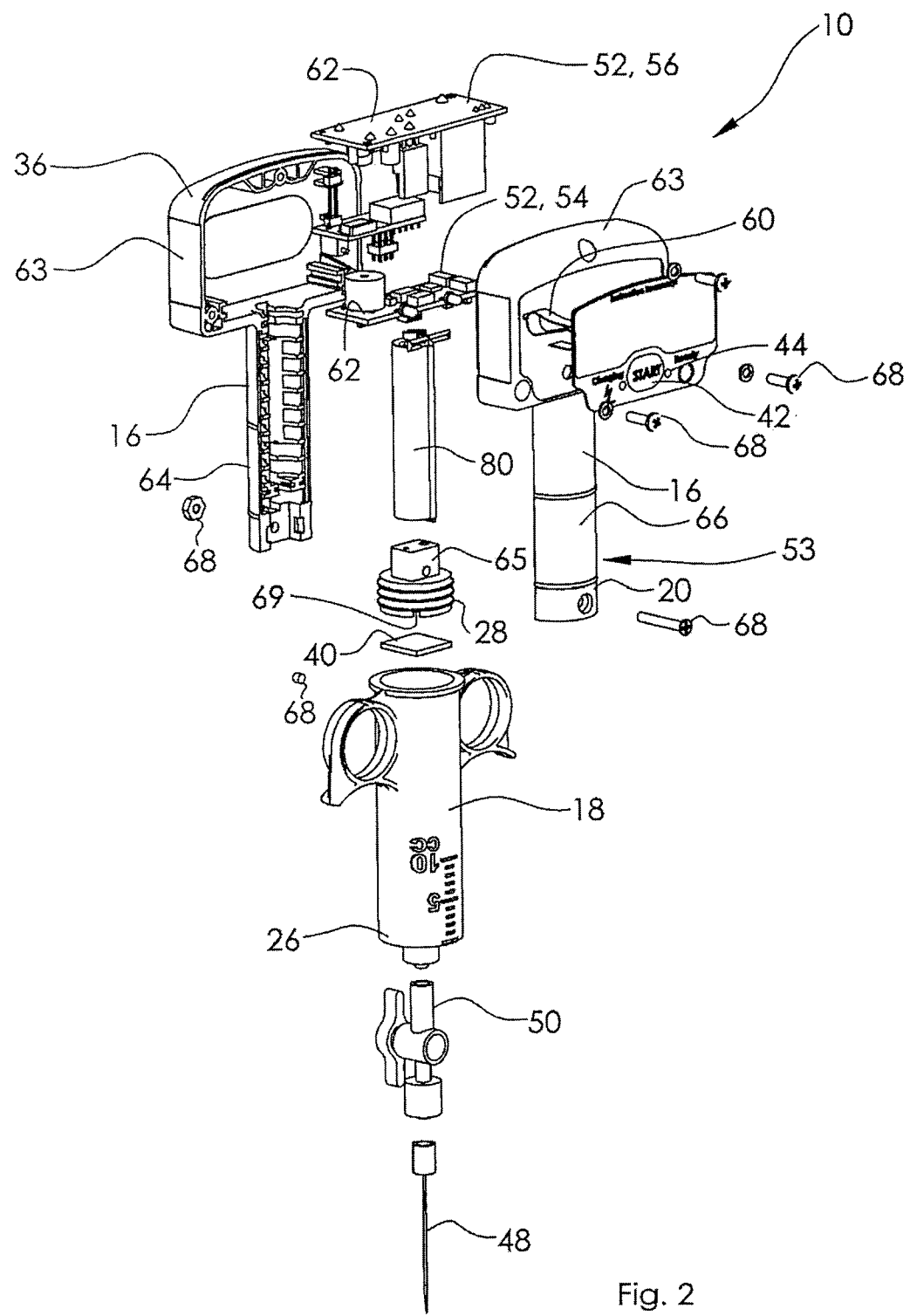
FIG. 2 is an exploded perspective view of the apparatus shown in FIG. 1.

Referring now to FIG. 2, a perspective exploded view of the embodiment of FIG. 1 of the present invention is shown. The apparatus 10 may further include a controller 52 for controlling the amount of material treated by the material treatment module 40. The controller 52 in one embodiment may include a timing circuit 54 for controlling the length of time the material treatment module 40 is permitted to treat material. In embodiments where the material treatment module 40 is an ozone generator and the precursor material is oxygen or air, the controller 52 may include an ozone circuit 56 for controlling the generation of ozone. The controller 52 is in electrical communication with the material treatment module 40. In one embodiment, the controller 52 is positioned within the plunger housing 53 and is used for controlling the amount of ozone generated by the material treatment module 40 which may be an ozone generator. It will be appreciated by those of skill in the art that the controller 52 may also include a relay circuit (not shown) in order for the controller 52 to properly control the function of the material treatment module 40.

A power source 80 is in electrical communication with the material treatment module 40 and the controller 52. The power source 80 can be direct current or alternating current. In one embodiment, the power source 80 includes a battery or a series of batteries positioned coaxially within the plunger 16. The controller 52 may include electronics capable of generating and delivering a high-voltage, high-frequency electrical signal to the material treatment module 40. The frequency of the signal can be between about one tenth of a kilohertz ("kHz") and about one thousand kHz. In one embodiment, the frequency is between about twenty kHz and about sixty kHz. The voltage of the electrical signal is between about one kilovolt and about twenty kilovolts. In one embodiment, the electrical signal is between about three kilovolts and about six kilovolts. In another embodiment, the power supply 80 can also supply an electric current with a voltage between about one volt and about thirty volts.

A switch 42 may be used to control the delivery of power by the power source 80. The switch and other electrical components communicate with each other electronically through wires or cables 60. When switch 42 is in the "on" position current is delivered to material treatment module 40, and when switch 42 is in the "off" position, no current is delivered. The switch 42 may any number of electrical switches known in the art. For example, the switch may be a toggle that allows a user to complete or break the circuit multiple times. In one embodiment, the switch is a pull tab configured such that when the pull tab is pulled out of the apparatus 10, the circuit is complete and current is delivered to the material treatment module 40. The timing circuit 54 may automatically stop the generation or delivery of current at a predetermined time. The controller 52 or individual components 54 and 56 of the controller 52 may also include a buzzer or light source to provide an audible or visual signal or display to indicate whether the apparatus 10 is on or off, or status of the material treatment module 40. The apparatus 10 may include a display. It will be appreciated by those of skill in the art that the electronic components of the apparatus 40 may be hardwired to a circuit board 62 as shown, or may be controlled by a programmable microprocessor (not shown).

The control elements and other electronics are contained with the handle 36 and body of the plunger 16. The plunger 16 may include a plunger housing 62 having a first part 64 and a second part 66. The housing 62 parts 64 and 66 together form a hollow interior in which the controller 52 and power source 80 are housed. An end cap 65 may be configured at the first end 20 of the plunger 16 to help hold the interior components in place. The end cap 65 may be configured with a seal 28 to provide sealing engagement with the interior of the barrel 18. The end cap 65 may also be configured to help control the telescoping engagement of the plunger 16 within the barrel 18. The plunger housing parts 64 and 66 may be secured together by fastening hardware 68 known in the art such as nuts, bolts, washers, set screws, and the like. The housing halves of the plunger 16 and other parts of the apparatus 10 such as the barrel 18 may be made of molded plastic and attached together in their operational state. The attachment may be accomplished in a number of ways including without limitation, adhesion or other types of bonding, welding, crimping, ultrasonic coupling, thermal coupling, and the like. The housings halves may also be configured to matingly engage each other by press fitting, snap fitting, and the like. Fasteners 68 of all types known in the art may also be used. It will be appreciated by those of skill in the art that the individual components may be made and combined in a variety of ways to practice the teachings of the invention. In one embodiment, the electronics and control components may be located in the barrel 18. In another embodiment, the electronics and control components may be located in a separate housing or module from the plunger 16 or barrel 18.

The plunger 16 and barrel 18 may be made from any suitable material that is substantially rigid, such as glass, stainless steel, polycarbonate, high density polyethylene, chlorinated polyvinylchloride, silicone, ethylene-propylene terpolymer, and fluoropolymer materials, such as polytetrafluoroethylene, fluorinated ethylene-propylene, and the like. It will be appreciated by those of skill in the art that the material used to make the apparatus 10 should be capable of functioning properly in light of the particular type of material treatment being accomplished by the material treatment module 40. For example, where the material treatment module 40 is an ozone generator, the plunger 16, barrel 18, and other components in contact with the material should be made of an inert material such as those listed above when exposed to ozone. When the material is being treated by heat, the material should be able to withstand the range of heat being used. Similarly, when the precursor material is being treated by ultraviolet light, the housing must be compatible to ultraviolet light.

The material treatment module 40 may be positioned within the end 20 of the plunger 16. In one embodiment, the material treatment module 40 is an electrochemical cell 40 having a cathode 70, anode 72, and an electrolyte (see FIG. 3). The chip 40 may be positioned within a cavity 69 configured within plunger 16. The material treatment module 40 is coaxial with the plunger and is open to and in communication with the chamber 14 defined by the first end 20 of the plunger 16 and the second end 26 of the barrel 18. Furthermore, it is to be understood that the material treatment module 40 may be disposed at any suitable position relative to the housing 12 of the apparatus 10. When the housing 12 is in the form of plunger 16/barrel 18 combination, the material treatment module 40 may be disposed at any suitable location between the first end 20 and the second end 22 of the plunger 16, or at any location between the first end 24 and the second end 26 of the interior of the barrel 18. In addition, the material treatment module 40 may also be disposed at any suitable location on an exterior surface of the device 10, or at a location outside the device where the material treatment module 40 is unattached to, but connected to, the device.

The material treatment device 40 may also be a corona discharge device. The material treatment module 40 may also be an ultraviolet ("UV") light source. In these embodiments, the power source 80, and electronic circuits 54, 56, circuit boards 62, cables 60 and controller 52 would be modified to allow for the proper function of the corona discharge device or UV light source. For example, the UV light source device, electronics would need to provide a wavelength of the light between about 100 nm and about 700 nm or between about 140 nm and about 200 nm.

In other aspects, the material treatment module 40 may be an open vessel for storing an ozonated gel and a heating element, such that activation of the heating element elevates a temperature of the gel causing desorption of ozone-oxygen mixture from the gel. The gel can be formed by sparging ozone through olive oil and then chilling the olive oil. The olive oil is chilled to a temperature of between about minus fifteen ° C. and about ten ° C. It will be appreciated by those of skill in the art that a variety of material treatment module 40 options may be used alone or in combination to practice the teachings of this invention.

A needle 48 attached to the outlet 46 may be of any desired material, length or gauge that may be desired according to the treated material being delivered. In one embodiment, the treated material is an oxygen-ozone mixture of therapeutic value, the details of which will be discussed in greater detail below. Where an oxygen-ozone mixture is being delivered into a herniated disc, the needle 48 can be a Chiba needle or Franceen needle or other suitable needle as will occur to those of skill in the art.

Figure 3:
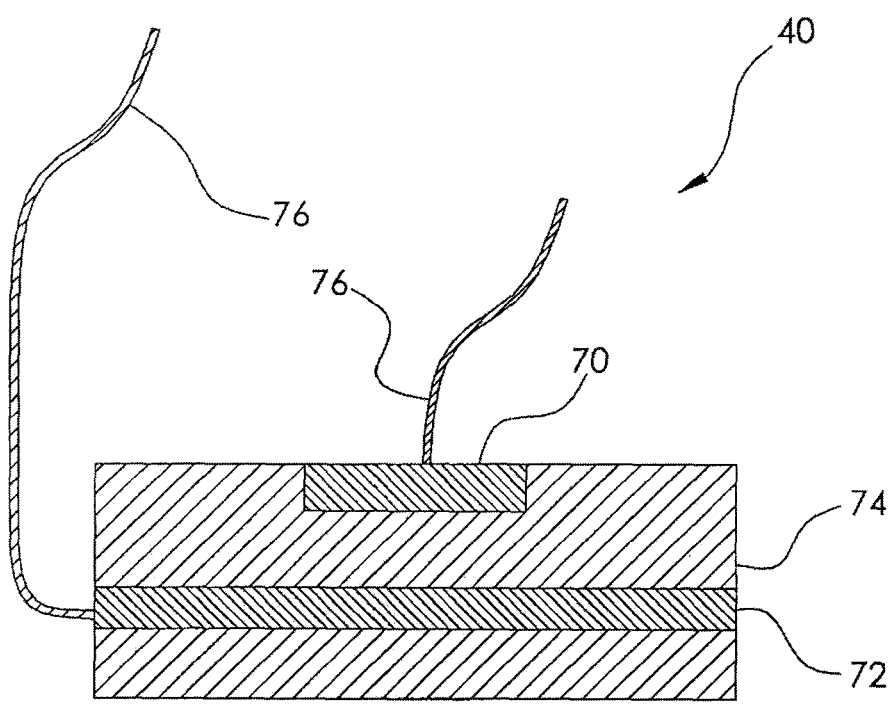
FIG. 3 is side cross-sectional view of the material treatment module of FIG. 1.

Referring now to FIG. 3, a more detailed view of a material treatment module 40 according to the present invention is shown. The material treatment module 40 may be an electrochemical cell comprising a cathode 70, an anode 72, and an electrolyte 74. At least a portion of the electrolyte 74 is positioned between the cathode 70 and the anode 72. The power source (not shown) provides voltage across the cathode 70 and the anode 72 by means of wires 76. In this embodiment, the material treatment module 40 can be an electrochemical ozone generator. An oxygen or air precursor material may interact with the material treatment module 40 such that an oxygen-ozone mixture is created. This mixture may be released from the electrochemical cell configuration of the material treatment module 40 by the electrolysis of water and the production of ozone and oxygen at the anode 72. In one embodiment, an electric current is used with an applied voltage between about three volts and about twenty volts. In another embodiment, a voltage between about two volts and about ten volts is used.

Figure 4:
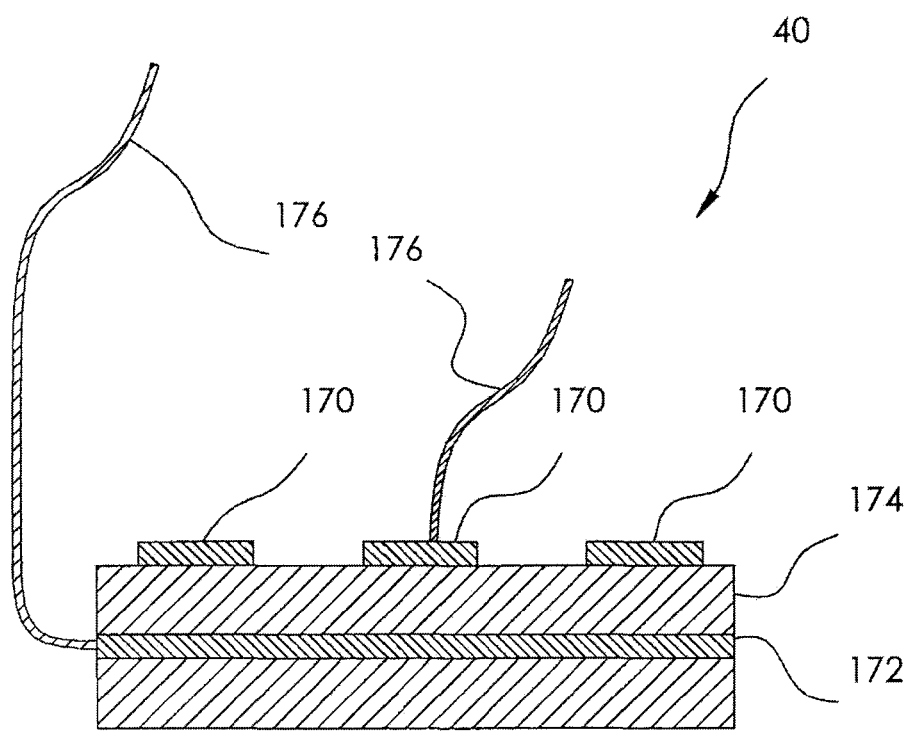
FIG. 4 is side cross-sectional view of another embodiment of the material treatment module of FIG. 1.

Referring now to FIG. 4 another embodiment of the material treatment generator 40 is illustrated. The material treating module 40 may be a surface-discharge corona. In this embodiment, a dielectric material 174 may be positioned between a pair of electrodes 170 and 172. Wires 176 may be used to connect to a discharge electrode 170 and an induction electrode 172. The electrodes are incorporated within a high purity alumina or silica dielectric 174. In one embodiment, the electrodes 170 and 172 contain without limitation, tungsten, platinum, nichrome, stainless steel or combination thereof. When a high-frequency, high-voltage power source is applied between the two electrodes 170 and 172, a stable high-frequency surface corona discharge takes place on the discharge electrode 170. An alternative embodiment utilizes a more traditional gap-discharge, corona material treatment module 40 that utilizes a glass dielectric and low-frequency high voltage power. In this configuration, the device 10 is used to create treated gas in the form of oxidizing gas. For example, the chamber 14 (see FIG. 1) may contain a starting gas in the form of pure oxygen gas. An oxygen-ozone mixture is released from the corona discharge device 40 by passing the oxygen-containing gas through an electrical field originating from device 40 at a frequency between about one-tenth kilohertz ("kHz") and about one thousand kHz. In one embodiment, a frequency between about twenty kHz and about sixty kHz is used. An electric current with a voltage between about one kilovolt and about twenty kilovolts and a more presently preferred voltage between about three kilovolts and about six kilovolts may also be used.

Referring now to FIGS. 5a and 5b, a device 10 according to the present invention is illustrated. In FIG. 5a, the device 10 is shown in a fill position where the first end 20 of the plunger 16 is retracted to fill the barrel 18. FIG. 5b shows the device 10 in a dispensing position, where the first end 20 of the plunger 16 is substantially with the barrel 18 such that the first end 20 of the plunger 16 is adjacent the second end 26 of the barrel 18.

The range of motion of the plunger 16 within the barrel 18, between the fill position and the dispensing position, may be defined by a groove 17 configured within the plunger 16. A stop 19 configured within the barrel 18 may be positioned within the groove 17 to control the maximum fill volume of the barrel 18. In another embodiment, multiple stops 19 can be incorporated to control both the fill and delivery volumes of the barrel 18. It will be appreciated by those of skill in the art that movement of the plunger 16 within the barrel 18 may be accomplished in a variety of ways known in the art. As stated above in connection with FIG. 1 the first end 20 of the plunger 16 and the second 26 of the barrel 18 form a chamber 14 or an accumulator. The chamber 14 volume decreases as the plunger is moved from a fill position to a dispensing position.

In use, the device 10 may be in a position such that the chamber (seen best in FIG. 1) is capable of holding a predetermined amount of material. This precursor material, as referred throughout the specification, may be any volume of material to be treated by the device. In most embodiments, it is a precursor liquid, gas, gel, or combination thereof that will be treated by the device in order to generate a beneficial or therapeutic agent. Precursor material may by drawn into the chamber 14 by attaching the outlet 46 or an apparatus attached the outlet 46 such as a needle to the source of precursor material and drawing the plunger 16 toward the fill position. Precursor material may also be charged into the chamber 14 from an external source attached to the device 10 or distant from the device 10. Precursor material may be charged into the chamber 14 before packaging of the device or after the user has obtained the device 10. It will be appreciated by those of skill in the art that there are a number of ways to charge the device 10 or chamber 14 with precursor material. The precursor material may include, without limitation, air, oxygen, water, nitrogen, carbon dioxide, chlorine, bromine, and combinations thereof. It may also include a salt solution, either alone or in combination with the foregoing. For example, the salt solution may include NaI, NaF, NaCl, NaBr, and the like. The precursor material may be in the form of a gas, liquid, gel, or combinations thereof. It will be appreciated that where the treated material is recycled for further treatment or further generation of therapeutic agent, or where it is desirous to treat a material twice in order to generate a higher concentration of some beneficial agent, then the precursor material may contain treated material.

The device 10 may then be activated by engaging a switch 42 (FIGS. 1 and 2), which allows activation of the power source 80 (FIG. 2), causing the material treatment module 40 to interact with the precursor material in the chamber 14. Depending upon the type of material treatment module 40 being used, activation of the device 10 creates or generates beneficial agent by treating the precursor material to create a treated material. For example, where the material treatment module 40 is an ozone generator in the form of a corona generator, and the precursor material is oxygen, activating the device 10 causes the material treatment module 40 to emit a field that interacts with the oxygen in the chamber 14 thereby creating ozone mixed with oxygen, which is a beneficial agent. Once the ozone generation cycle is complete, the plunger 16 is depressed to deliver ozone from the outlet 46. Of note, in the one embodiment the stroke of plunger 16 is chosen so that, when fully depressed, material treatment module 40 may come into close proximity of the second end 26 of the barrel 18, but without actually coming into contact therewith.

As used throughout the specification, treated material may be material that has been altered or modified in any way by operation of the device 10. Thus, the terms precursor material and treated material refer to material at different stages of single operation of the device 10. Using the example above, where the precursor material is oxygen and the material treatment module 40 is an ozone generator, activation of the device 10 will create a treated material consisting of a mixture of ozone and oxygen. If this mixture were stored and later charged into the device for a second application, this treated mixture would then be the precursor material for the second application of the device 10.

The treated material is the therapeutic agent desired to be delivered to a patient. The treated material may include without limitation, ozone, oxygen, nitric oxide(s), chlorine, fluorine, chlorine dioxide, iodine, carbon dioxide, bromine, bromine dioxide, oxygen radicals; hydroxyl radicals; ionic oxygen; oxygen treated with energy and combinations thereof. At least a portion of the treated material may also include precursor material. The treated material may also include inert gases which can include, but are not limited to, nitrogen, helium, carbon dioxide, and/or combinations thereof.

Figures 6A, 6B, 6C:
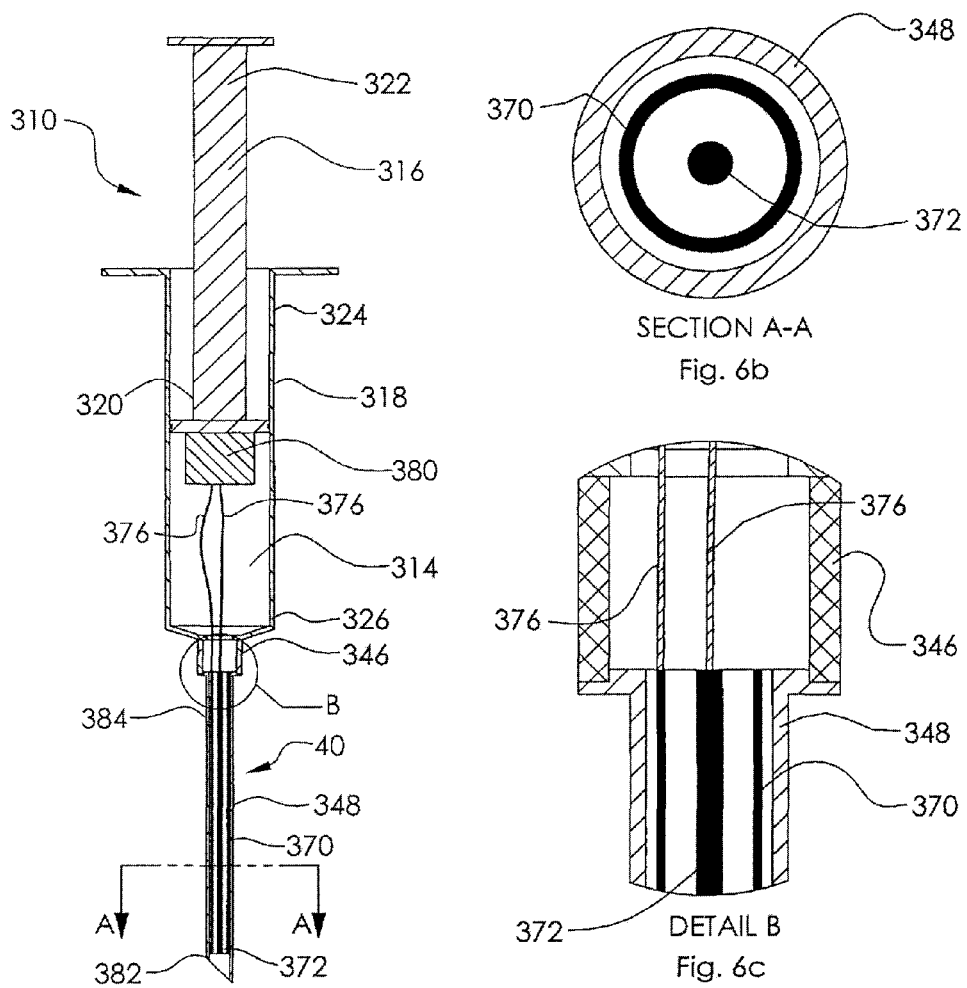

Referring now to FIG. 6a, another embodiment of the device 310 is illustrated. The device 310 includes a plunger 316 and a barrel 318 that define a chamber 314 for holding precursor material. The plunger 316 has a first end 320 and a second end 322. The barrel 318 has a first end 324 that is open for receiving the first end 320 of the plunger 316 such that the plunger 316 movably engages the barrel 318. The barrel 318 also includes a second end 326. The second end 326 of the barrel 318 may be configured with an outlet 346 that serves as the outlet 346 for the chamber 314. A needle 348 may include a first end 382 and a second end 384. The second end 384 of the needle 348 may be attached to the outlet 346 using a Luer or other mechanical connection or fitting.

In this embodiment, the material treatment module 40 is within the needle 348 or is the needle 348 itself. As can best be seen in FIG. 6b, a cross sectional view of FIG. 6a taken along line A-A, and FIG. 7c, a blown up view of area B, the needle 348 utilizes a flow-through electrochemical cell to create treated material in the form of a therapeutic agent. The electrochemical cell needle 348 includes an anode 370 and a cathode 372. Electric current is delivered to the anode 370 and cathode 372 by wires 376 attached to a power source 380. The chamber 314 is charged with precursor material or precursor or electrolyte 374. As with other embodiments disclosed herein, the electrochemical reaction between the material treatment module 340 and the precursor material can be controlled by the selection of electrode or electrolyte material. The electrodes 370 and 372 affect the electrochemical kinetics of the electroxidation/electroreduction reaction at the electrode 370 and 372.

The power source is initiated to polarize the anode 370 and cathode 372 which generates therapeutic agent by electrooxidizing or electroreducing the precursor material as it is plunged out the chamber 314 and into the needle 348. In another embodiment, the anode 370 is the metallic wall of the needle. The anode 370 and cathode 372 may be reversed for all embodiments. As discussed above, the timing and control of the applied voltage and/or current power source control the amount of beneficial agent that is produced by the material treatment module 40, and may be manual or automatic (i.e. programmable microprocessor controlled).

It will be appreciated by those of skill in the art that for ease of operations, the wires can be conductors that are printed on the inside of the chamber 314. In one embodiment the wires 376 are insulated and the electrodes 370 and 372 are conductive and selective for the desired beneficial agent. For gas precursors, the electrodes 370 and 372 may be tungsten, platinum, stainless steel, nichrome, or aluminum configured in the needle 348. It will be appreciated that the material treatment module 40 in the needle 348 configuration may also be set up as corona discharge device in a manner similar to a traditional gap-discharge, corona discharge devices. In this configuration, the needle would gas treating module that utilize a glass dielectric on the high-voltage electrode and would be powered by low-frequency, high-voltage power. For liquid precursors, similar electrodes are used, however they are powered by low voltages, and do not require a dielectric like the high voltage electrodes.

Figure 7A:
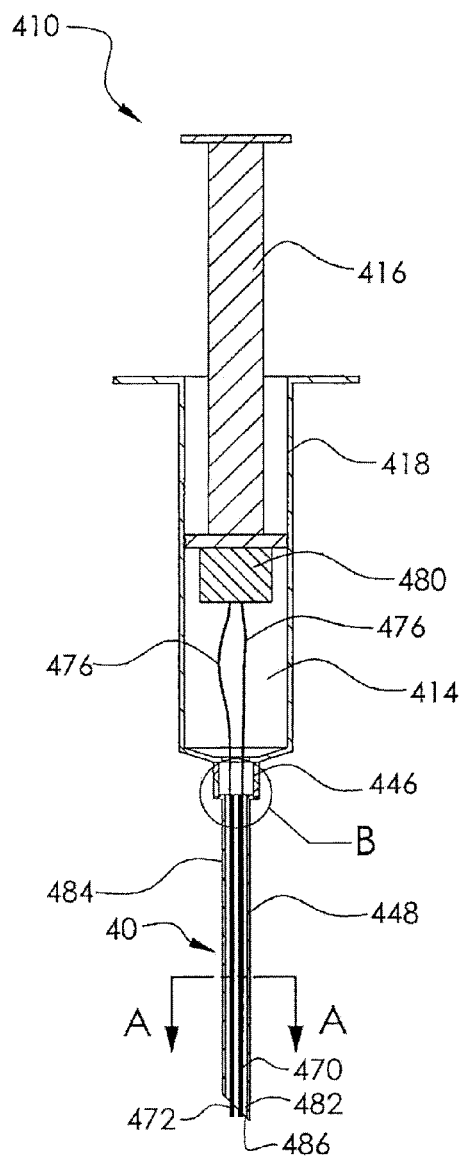
FIG. 7a is a cutaway plan view of an alternative embodiment of the invention.

Referring now to FIG. 7a, another embodiment of the device 410 according to the present invention is shown. The device 410 includes a plunger 416 and a barrel 418 that define a chamber 414 for holding precursor material. The plunger 416 has a first end 420 and a second end 422. The barrel 418 has a first end 424 that is open for receiving the first end 420 of the plunger 416 such that the plunger 416 movably engages the barrel 418. The barrel 418 also includes a second end 426. The second end 426 of the barrel 418 may be configured with an outlet 446 that serves as the outlet 446 for the chamber 414. A needle 448 may include a first end 482 and a second end 484. The second end 484 of the needle 448 may be attached to the outlet 446 using a Luer or other mechanical connection or fitting.

Figure 7B:
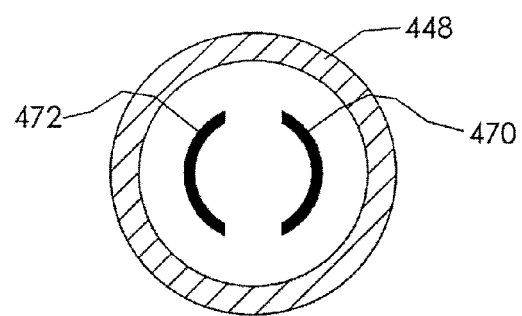
FIG. 7b is cross-sectional plan view of FIG. 7a taken along line A-A.
Figure 7C:
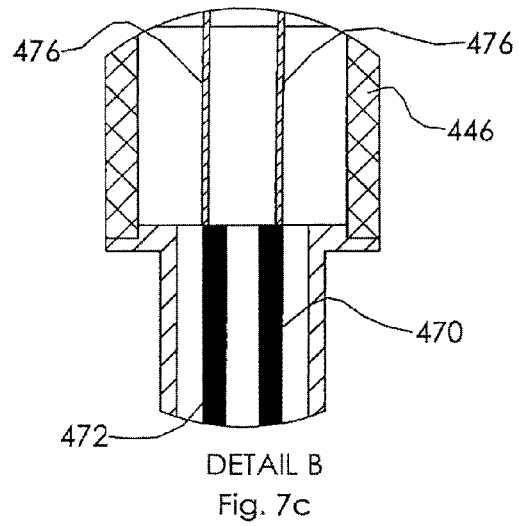

In this embodiment, the material treatment module 40 is the needle 448. As can best be seen in FIG. 7b, a cross sectional view of FIG. 7a taken along line A-A, and FIG. 7c, a magnified view of area B, the needle 448 utilizes a flow-through electrochemical cell to create treated material in the form of a therapeutic agent. The electrochemical cell needle 448 includes an anode 470 and a cathode 472. Electric current is delivered to the anode 470 and cathode 472 by wires 476 attached to a power source 480. The chamber 414 is charged with precursor material or precursor or electrolyte 374.

In this embodiment, the needle 480 houses electrodes 470 and 472 that are used to produce a beneficial agent in situ, or in other words, within the body. In this embodiment, additional electrolyte may or may not be supplied in chamber 414. The electrodes 470 and 472 extend beyond the opening 486 to have greater access to body fluid for generating in situ treated material which can be a beneficial agent. It will be appreciated that the plunger 416/barrel 418 configuration is not necessary for this application because the treated material is generated beyond the end 486 of the needle 448. However, the syringe-type configuration may be desirable to provide additional saline solution or other liquid precursors by plunging of the plunger 416 into the barrel 418 for patients that are dehydrated or to areas of the body that don't have much material. The first end 482 of the needle may have a protective shield or shroud (not shown) that protects the electrodes 470 and 472 from being damaged upon insertion.

A method of dispensing a material using a handheld dispensing apparatus is also disclosed. A dispensing apparatus or device 10, 310, 410, as discussed above may be used to dispense the material. The method includes collecting a precursor material in the chamber 14, 314, 414. The material treatment module 40, 340, 440 is activated. The precursor material collected in the chamber 14, 314, 414 is treated by the material treatment module to create a treated material. The needle 48, 348, 448 is positioned within a body. The treated material is then dispensed out of the device 10, 310, 410 or chamber into the body through the needle.

In one embodiment, the precursor material may include, without limitation, air, oxygen, water, nitrogen, carbon dioxide, chlorine, bromine, iodine, flourine and combinations thereof. It may also include a salt solution, either alone or in combination with the foregoing. For example, the salt solution may include NaI, NaF, NaCl, NaBr, and the like. It will be appreciated by those of skill in the art that the term salt solution includes compounds formed when the hydrogen of an acid is replaced by a metal.

Activating the material treatment module 40 includes engaging a switch to allow power from a power source to be delivered to the material treatment module. The method may also include deactivating the material treatment module, either manually or automatically. The method may also include detecting an amount of material treated by the material treatment module to determine when to shut off the module 40 or device 10. This may be accomplished by monitoring a display.

In embodiments, where the housing is a syringe configuration with a plunger 16, 316, 416 movably engaged within a barrel 18, 318, 418, dispensing the material may include moving the plunger relative to the barrel such that treated material is delivered through the needle into the body.

Without further elaboration, it is believed that one skilled in the art can use the preceding description to utilize the present disclosure to its fullest extent. The examples and embodiments disclosed herein are to be construed as merely illustrative and not a limitation of the scope of the present disclosure in any way. It will be apparent to those having skill in the art that changes may be made to the details of the above-described embodiments without departing from the underlying principles of the disclosure provided herein. In other words, various modifications and improvements of the embodiments specifically disclosed in the description above are within the scope of the appended claims. Note that elements recited in means-plus-function format are intended to be construed in accordance with 35 U.S.C. §112 ¶6. The scope of the invention is therefore defined by the following claims.

The invention claimed is:

1. A handheld dispensing apparatus comprising:
a plunger;
a barrel configured to receive and movably engage the plunger, the plunger and the barrel defining a chamber for retaining a precursor material;
an outlet in material communication with said chamber; and
a needle comprising a material treatment module in communication with the outlet, said material treatment module configured to treat said precursor material to create a treated material, wherein the material treatment module comprises an electrochemical cell comprising an anode, a cathode, and an electrolyte, at least a portion of said electrolyte positioned between the anode and the cathode.

2. The apparatus of claim 1, wherein the precursor material comprises one of the group consisting of air, oxygen, water, salt solution, nitrogen, carbon dioxide, chlorine, bromine, fluorine, iodine, and combinations thereof.

3. The apparatus of claim 1, wherein at least a portion of the treated material comprises one of the group consisting of: ozone, oxygen, oxygen radicals, oxygen treated with energy, hydroxyl radicals, ionic oxygen, nitric oxide, chlorine, fluorine, chlorine dioxide, nitrogen, helium, iodine, carbon dioxide, bromine, bromine dioxide, and combinations thereof.

4. The apparatus of claim 1, wherein at least a portion of the treated material comprises precursor material.

5. The apparatus of claim 1, wherein the chamber is less than about 150 cubic centimeters.

6. The apparatus of claim 5, wherein the chamber is greater than about 0.1 cubic centimeters.

7. The apparatus of claim 1, further comprising a power source in electrical communication with the material treatment module.

8. The apparatus of claim 7, wherein the power source comprises a battery.

9. The apparatus of claim 7, further comprising a switch for controlling the delivery of power by the power source.

10. The apparatus of claim 7, further comprising a controller in communication with the power source for controlling the amount of material treated by the material treatment module.

11. The apparatus of claim 10, wherein the controller is a timing circuit for controlling the length of time the material treatment module is permitted to treat material.

12. The apparatus of claim 7, wherein the power source provides voltage across the anode and the cathode.

13. The apparatus of claim 7, wherein the power source is coaxially mounted to the plunger.

14. The apparatus of claim 7, wherein the power source is mounted to an end of the plunger within the chamber defined by the plunger and the barrel.

15. The apparatus of claim 1, wherein the material treatment module comprises an ozone generator.

16. The apparatus of claim 1, further comprising a display to indicate a status of the material treatment module.

17. The apparatus of claim 1 further comprising a valve for controlling the movement of material between the chamber and the needle.

18. A handheld dispensing apparatus comprising:
a plunger;
a barrel configured to receive and movably engage the plunger, the plunger and the barrel defining a chamber for retaining a precursor material;
an outlet in material communication with said chamber;
a needle comprising an ozone generator in communication with the outlet, said ozone generator configured to treat said precursor material to create a treated material;
a power source mounted to the plunger, wherein the power source is in electrical communication with the ozone generator; and
a switch for controlling the delivery of power by the power source.

19. The apparatus of claim 18, wherein the power source is coaxially mounted to an end of the plunger within the chamber defined by the plunger and the barrel.

20. The apparatus of claim 18, wherein the ozone generator comprises a corona cell comprising a dielectric material positioned between a pair of electrodes.

* * * * *